(12) United States Patent
Sullivan et al.

(10) Patent No.: US 7,510,734 B2
(45) Date of Patent: Mar. 31, 2009

(54) **SKIN TREATMENT METHOD WITH *LACTOBACILLUS* EXTRACT**

(75) Inventors: Michael Sullivan, Holbrook, NY (US); Steven F. Schnittger, Huntington Station, NY (US); Thomas Mammone, Farmingdale, NY (US); Earl C. Goyarts, Commack, NY (US)

(73) Assignee: E-L Management Corporation, New York, NY (US)

( * ) Notice: Subject to any disclaimer, the term of this patent is extended or adjusted under 35 U.S.C. 154(b) by 330 days.

(21) Appl. No.: 11/070,810

(22) Filed: Mar. 2, 2005

(65) Prior Publication Data

US 2005/0196480 A1    Sep. 8, 2005

(51) Int. Cl.
*A61K 35/00* (2006.01)
*A01N 63/00* (2006.01)

(52) U.S. Cl. .................................... 424/780; 424/93.45

(58) Field of Classification Search ........................ None
See application file for complete search history.

(56) References Cited

U.S. PATENT DOCUMENTS

| | | | |
|---|---|---|---|
| 4,883,673 A * | 11/1989 | Gonzalez | 514/44 |
| 6,710,219 B2 * | 3/2004 | Persson et al. | 604/359 |
| 6,761,885 B1 * | 7/2004 | Håkansson et al. | 424/93.45 |
| 2003/0091540 A1 * | 5/2003 | Ahmad et al. | 424/93.3 |
| 2003/0143262 A1 * | 7/2003 | Brusk et al. | 424/443 |
| 2004/0052759 A1 | 3/2004 | Sawaki et al. | |
| 2004/0067573 A1 * | 4/2004 | Connolly et al. | 435/252.1 |
| 2004/0243076 A1 * | 12/2004 | Husmark et al. | 604/358 |

FOREIGN PATENT DOCUMENTS

| | | | |
|---|---|---|---|
| EP | 1 097 700 A1 | 5/2001 | |
| EP | 1366736 | * | 12/2003 |
| FR | 2718752 | 10/1995 | |
| JP | 61087614 | 5/1986 | |
| JP | 63-179829 | 7/1988 | |
| JP | 01-210490 | 8/1989 | |
| JP | 2804312 B2 | 5/1991 | |
| JP | 3112983 B2 | 12/1992 | |
| JP | 05286846 | 11/1993 | |
| JP | 10182409 | 7/1998 | |
| JP | 2001-097842 | 4/2001 | |
| JP | 2001112466 | 4/2001 | |
| JP | 2001271096 | 10/2001 | |
| JP | 2001354570 | 12/2001 | |
| JP | 2002037739 | 2/2002 | |
| JP | 2002037742 | 2/2002 | |
| JP | 2002191387 | 7/2002 | |
| KR | 2000060083 | 10/2000 | |
| KR | 2001107152 | 12/2001 | |
| KR | 20030072812 | 9/2003 | |
| RU | 2185842 | * | 7/2002 |
| WO | WO 99/07332 | 2/1999 | |
| WO | WO 02/060395 | * | 8/2002 |
| WO | WO02/094296 | 11/2002 | |
| WO | WO03/068250 | 8/2003 | |

OTHER PUBLICATIONS

Marsalkova Slavka et al. Berliner und Munchener tierarztliche Wochenschrift. Mar.-Apr. 2004. vol. 117, No. 3-4, pp. 145-147, MEDLINE Abstract enclosed.*
Schnittger et al. 23rd IFSCC Intl. Congress. Oct. 24-27, 2004. Poster 91, KOSMET Abstract enclosed.*
Anonymous author. Forum Cosmeticum 2002. Apr. 24-26, 2002. Poster. KOSMET Abstracdt enclosed.*
Database Kosmet on STN, AN 28718. Yi, S. "Multifunctional Activities of Cultured Extracts from *Lactobacillus plantarum* M1 as Cos Ingredients". IFSCC Conf. Sep. 2003, Seoul, KR 2003, Seoul, KR, Poster 57. Abstract only.
Lehrer, et al., Defensins: Endogenous Antibiotic Peptides of Animal Cels, Cell, vol. 64, 229-230, Jan. 25, 1991.
Lehrer, et al., Defensins: Antimicrobial and Cytotoxic Peptides of Mammalian Cells, Ann. Rev. Immunol. 1993, 11:105-28, pp. 105-128.
Porter, et al., Broad-Spectrum Antimicrobial Activity of Human Intestinal Defensin 5—Infection and Immunity, Jun. 1997, vol. 65, No. 6, pp. 2396-2401.
Frosch, et al., A Method for Appraising the Stinging Capacity of Topically Applied Substance—J. Soc. Cosmet. Chem. 28:197-209, May 1977.
King, A.E., et al; "Regulation of natural antibiotic expression by inflammatory mediators and mimics of infection in human endometrial epithelial cells"; Molecular Human Reproduction; vol. 8; No. 4; pp. 341-349; 2002.
Kawai, K., et al.; "Expression of functional Toll-like receptor 2 on human epidermal keratinocytes"; Journal of Dermatological Science; vol. 30; pp. 185-194; 2002.
Molin, Goran; "Probiotics in foods not containing milk or milk constituents, with special reference to *Lactobacilus plantarum* 299v[1-3]"; American Journal of Clinical Nutrition; 73 (suppl.); 380S-385S; 2001.
PCT International Search Report; International Authority, Or The Declaration; Completion Date: Oct. 6, 2005; Date of Mailing: Nov. 1, 2005.
PCT Written Opinion Of the International Searching Authority; Or the Declaration; Completion Date: Oct. 22, 2005; Date of Mailing: Nov. 1, 2005.

* cited by examiner

*Primary Examiner*—Christopher R. Tate
(74) *Attorney, Agent, or Firm*—Yongzhi (Mimi) Yang (57) ABSTRACT

The present invention relates to a method of stimulating beta-defensins in skin cells which comprises applying to the skin cells an effective amount of a *Lactobacillus* extract or active fraction thereof.

4 Claims, 9 Drawing Sheets

**Effect of 10% *Lactobacillus* formulation on papules and pustules**

Figure 9a

**Effect of 10% *Lactobacillus* formulation on open and closed comedones**

SKIN TREATMENT METHOD WITH *LACTOBACILLUS* EXTRACT

FIELD OF THE INVENTION

The invention relates to the field of cosmetic compositions and uses thereof. In particular, the invention relates to cosmetic compositions that can be used to stimulate production of beta-defensins in skin cells.

BACKGROUND OF THE INVENTION

Antimicrobial peptides are a naturally occurring defense system that is widespeard throughout a number of plant and animal species. One type of antimicrobial peptide found in vertebrates is the group of molecules known as defensins. Structurally, these molecules are united by the presence of six invariant cysteines and three intramolecular cystine disulfide bonds. (Lehrer et al., *Cell* 64: 229-230, 1997; *Ann. Rev. Immunol.* 11: 105-128, 1993). Two different classes of defensins have been observed. The first are classic defensins, that are stored in neutrophils and macrophages, and which are used to inactivate microbes that these cells have phagocytosed. The second class comprises beta-defensins, which have been isolated from mammalian lung and skin cells. These molecules are known to exhibit a wide range of antibiotic activity against pathogens, such as bacteria, fungi, and viruses (Porter et al., *Infect. Immun.* 65(6): 2396-2401, 1997).

As noted above, skin cells have been shown to produce beta-defensins. It has also been shown that the exposure of skin cells to bacterial cells, in particular *Pseudomonas*, even in an inactivated state, can induce the production of beta-defensin-2 in keratinocytes. Presumably this response is present in the skin to protect it from the onslaught of noxious stimuli, particularly in the form of microbes. It has been theorized that the stimulatory components of gram positive bacteria may be lipoteichoic acid or peptidoglycans, while LPS, an endotoxin, is responsible for eliciting the beta-defensin response to gram-negative bacteria.

It would be useful if it were possible to elicit this response at will from the skin with a safer stimulant, so as to provide a consistent protective agent on the skin. To date, however, the use of a safer bacterium than *Pseudomonas* to elicit skin cell beta-defensins has not been suggested. The present invention now provides a method for stimulating the production of beta-defensins in skin cells with a cosmetically acceptable non-pathogenic bacterium.

SUMMARY OF THE INVENTION

The invention relates to a method for stimulating the production of beta-defensins in skin cells comprising applying to the skin cells a stimulatory effective amount of a *Lactobacillus* extract. The invention also relates to a method of protecting skin against damage due to noxious stimuli by application of a stimulatory effective amount of a *Lactobacillus* extract.

BRIEF DESCRIPTION OF THE FIGURES

FIGS. 1 and 2 illustrate a visual quantitation of the ribosomal 28S RNA band for various samples of *Lactobacillus* extract fractions. FIG. 1, lane identification: 1, 1844 filtrate 5×10E9; 2, 1839 ferment 10E8; 3, 1839 retentate 5×10E10; 4, 1839 filtrate 10E9; 5, 1839 filtrate 5×10E9; 6, 1839 filtrate 10E10; 7, 1839 HXCH 10E10; 8, lambda Hind III. FIG. 2, lane identification: 1, lambda Hind III; 2, Untreated B; 3, 1844 ferment 5×10E9; 4, 1844 retentate 10E10; 5, 1844 retentate 5×10E10; 6, 1844 filtrate 5×10E10; 7, 1844 HXCH 10E9; 8, 1844 HXCH 5×10E9.

FIG. 4 illustrates the effect of various fractions of *Lactobacillus* extracts 1839 and 1844 on internal control 18S Ribosomal mRNA levels after 48 hrs of NHEK growth. The light gray samples are the untreated. The green samples correspond to unprocessed 1844 ferments ($10^8$, $10^9$, $5 \times 10^9$ or $10^{10}$ bacteria). The light green samples correspond to the 1839 unprocessed ferments ($10^8$, $10^9$ or $10^{10}$). The red samples correspond to the 1844 heat-exchanged samples ($10^9$, $5 \times 10^9$ or $10^{10}$). The yellow samples correspond to the 1839 heat-exchanged samples ($10^8$, $10^9$ or $10^{10}$). The blue samples correspond to the 1844 filtrates ($10^9$, $5 \times 10^9$ or $10^{10}$). The light blue samples correspond to the 1839 filtrates ($10^9$, $5 \times 10^9$ or $10^{10}$). The filtrate consists of water-soluble cell debris, which can pass through the cross-flow filter. The purple samples correspond to the 1844 retentates ($10^9$, $10^{10}$ or $5 \times 10^{10}$). The pink samples correspond to the 1839 retentates ($10^9$, $10^{10}$ or $5 \times 10^{10}$). The retentate contains water-insoluble cell debris, which does not pass through the cross-flow filter (0.22µ). Samples having a "*" are independent treatments.

FIG. 5 illustrates the effect of various fractions of *Lactobacillus* extracts 1839 and 1844 on human beta defensin-2 mRNA levels after 48 hrs of NHEK growth. The light gray samples are the untreated. The green samples correspond to unprocessed 1844 ferments ($10^8$, $10^9$, $5 \times 10^9$ or $10^{10}$ bacteria). The light green samples correspond to the 1839 unprocessed ferments ($10^8$, $10^9$ or $10^{10}$). The red samples correspond to the 1844 heat-exchanged samples ($10^9$, $5 \times 10^9$ or $10^{10}$). The yellow samples correspond to the 1839 heat-exchanged samples ($10^8$, $10^9$ or $10^{10}$). The blue samples correspond to the 1844 filtrates ($10^9$, $5 \times 10^9$ or $10^{10}$). The light blue samples correspond to the 1839 filtrates ($10^9$, $5 \times 10^9$ or $10^{10}$). The filtrate consists of water-soluble cell debris, which can pass through the cross-flow filter. The purple samples correspond to the 1844 retentates ($10^9$, $10^{10}$ or $5 \times 10^{10}$). The pink samples correspond to the 1839 retentates ($10^9$, $10^{10}$ or $5 \times 10^{10}$). The retentate contains water-insoluble cell debris, which does not pass through the cross-flow filter (0.22µ). Samples having a "*" are independent treatments.

FIG. 6 illustrates the effect of other materials on Human beta defensin-2 mRNA levels after 48 hrs of NHEK growth, in comparison with the effect of *Lactobacillus* fractions. The tight gray samples are the untreated. The white sample is the Mangiferin (#4245) from MMP. The red samples correspond to the *Pseudomonas aeruginosa* samples ($10^5$, $10^6$ or $10^7$ bacteria). The teal samples correspond to a mix of agar grown *Lactobacillus* ($10^8$ bacteria) and agar grown *Pseudomonas* ($10^5$ or $10^6$ bacteria). The yellow sample corresponds to agar grown *Lactobacillus* ($10^8$). The blue samples correspond to the 24 hr unprocessed *Lactobacillus* ferment. The turquoise samples correspond to the unprocessed heat exchange sample. The dark green samples correspond to the filtrate. The filtrate consists of water-soluble cell debris, which can pass through the cross-flow filter (0.22µ). The light green samples correspond to the retentate. The retentate contains water-insoluble cell debris, which does not pass through the cross-flow filter (0.22µ).

DETAILED DESCRIPTION OF THE INVENTION

The invention is based on the observation that extracts of *Lactobacillus* can stimulate the production of beta-defensins in skin cells, generally in a dose-dependent manner. In particular, it has been noted that several different forms of *Lactobacillus* extract, including extracts containing both water soluble and water insoluble materials are able to elicit beta-defensin production in skin cell cultures. A schematic representation of the preparation of the various treatment samples is provided in FIG. 1. In summary, each of the unprocessed extract samples, as well as heat-fractionated and cross-filtered filtrate and retentate, exhibits some level of activity in stimulating beta-defensin production. Activity is most prominent in samples comprising cell concentrations in the range of at least about $1\times10^9$ to about $1\times10^{10}$. Extracts grown on both beef-based and bean-based broth have been shown to possess beta-defensin inducing activity.

*Lactobacillus* extracts have been previously used in cosmetic applications for a variety of purposes. For example, WO9907332 discloses the use of *Lactobacillus acidophilus* strains to produce ferments said to be useful in protecting skin against pathogenic microflora. EP 1097700 discloses a hair growth composition containing a *Lactobacillus bulgaricus* filtrate. WO 02/60395 relates to a product prepared by rice fermented with *Lactobacillus plantarum*, which product is said to be useful in skin care products as an emulsifier. JP 3112983 discloses a combination of ground *Lactobacillus* cells and fermentation liquid for moisture retention in skin. JP 2002037742 describes a *Lactobacillus* fermented metabolite, useful for skin fatigue and anti-ageing. JP 2002037739 discloses an "immunomodulator" which is a metabolite of fermentation of lactic acid bacteria on various substrates. JP 2804312 describes a soy milk fermented by *Lactobacillus* species, said to be useful for whitening. However, to Applicants' knowledge, *Lactobacillus* has not previously been used to stimulate the productions of beta-defensins in skin cells.

Different forms of the extract can be used in the compositions and methods of the invention, as the pertinent activity can be found in various fractions. For example, a boiled but further unprocessed extract can be used; however, similar activity can also be obtained using a heat exchange-treated (flash-heated and flash-cooled) extract, in which the bacterial cells are broken up. In addition, a heat exchange-treated extract further subjected to cross-flow filtration with a 0.22μ filter will yield a filtrate (containing water soluble cellular debris) and a retentate (containing water-insoluble cellular debris) each of which exhibit activity defensin-inducing activity. Any one or a combination of these extracts or fractions can be used.

In practical use, the *Lactobacillus* extracts are combined in virtually any type of topically useful vehicle, in amounts capable of stimulating the production of beta-defensins. The carriers will be those that are pharmaceutically or cosmetically acceptable, that is, a vehicle, for either pharmaceutical or cosmetic use, intended for application to external body surfaces, such as skin, hair or nails, which vehicle delivers the active components to the intended target and which will not cause harm to the average human or other recipient organisms when applied to the surface intended to be treated. As used herein, "pharmaceutical" or "cosmetic" will be understood to encompass both human and animal, preferably mammalian, pharmaceuticals or cosmetics with which the active component is compatible, e.g., a gel, a cream, a lotion, an ointment, a mousse, a spray, a solid stick, a powder, a suspension, a dispersion, and the like. Techniques for formulation of various types of vehicles are well known to those skilled in the art, and can be found, for example, in Chemistry and Technology of the Cosmetics and Toiletries Industry, Williams and Schmitt, eds., Blackie Academic and Professional, Second Edition, 1996 *Harry's Cosmeticology*, Eighth Edition, M. Reiger, ed. (2000), and *Remington: The Science and Practice of Pharmacy*, Twentieth Edition, A. Gennaro, ed., (2003), the contents of each of these being incorporated herein by reference. Any typical composition that is useful for topical delivery, for example, aqueous dispersions, anhydrous compositions, emulsions (oil or silicone-in-water, water-in-oil or silicone, multiple emulsions, microemulsions, nanoemulsions), can be employed, provided the components are compatible with the active extract or fraction. The composition can also contain other topically useful components which may enhance or complement the activity of the composition. The choice of accompanying ingredients in the composition will also depend upon the intended use of the compositions. Standard topically useful ingredients can be found in, for example, The International Cosmetic Ingredient Dictionary and Handbook, 10th Edition, 2004, the contents of which are incorporated herein by reference. Examples of useful categories of topically acceptable ingredients that may be combined with the extracts include, but are not limited to: fragrances or essential oils; pigments or colorants; formulation aids such as anti-caking agents, anti-foaming agents, fillers and bulking agents, thickeners, gellants, structuring agents and emulsion stabilizers; surfactants and emulsifiers; film-forming agents to enhance adhesion and retention on the intended target; propellants, preservatives and pH adjusters and neutralizing agents. Other components which may be useful in combination with the extracts are those ingredients that provide an additional benefit to the keratinous surface to which the composition will be applied, hereinafter referred to as "skin benefit agents". Examples of such skin benefit agents include, but are not limited to, astringents, such as clove oil, menthol, camphor, eucalyptus oil, eugenol, menthyl lactate, witch hazel distillate; antioxidants or free-radical scavengers, such as ascorbic acid, its fatty esters and phosphates, tocopherol and its derivatives, N-acetyl cysteine, sorbic acid and lipoic acid; anti-acne agents, such as salicylic acid and benzoyl peroxide; antimicrobial or antifungal agents such as caprylyl glycol, triclosan, phenoxyethanol, erythromycin, tolnaftate, nystatin or clortrimazole; chelating agents, such as EDTA; topical analgesics, such as benzocaine, lidocaine or procaine; anti-aging/anti-wrinkle agents, such as retinoids or hydroxy acids; skin lightening agents, such as licorice, ascorbyl phosphates, hydroquinone or kojic acid), skin-conditioning agents (e.g., humectants, including miscellaneous and occlusive), antiirritants, such as cola, bisabolol, aloe vera or panthenol, anti-inflammatories, such as hydrocortisone, clobetasol, dexamethasone, prednisone, acetyl salicylic acid, glycyrrhizic acid or glycyrrhetic acid; anti-cellulite agents, such as caffeine and other xanthines; humectants, such as alkylene polyols or hyaluronic acid; emollients, such as oily esters or petrolatum; sun protecting agents (organic or inorganic), such as avobenzone, oxybenzone, octylmethoxycinnamate, titanium dioxide or zinc oxide; exfoliating agents (chemical or physical), such as N-acetyl glucosamine, mannose phosphate, hydroxy acids, lactobionic acid, peach kernels, or sea salts; self-tanning agents, such as dihydroxyacetone; and biologically active peptides, such as palmitoyl pentapeptide or argireline. These supplemental skin benefit agents will be used in the amounts normally known to be effective for that active when used for the intended purpose.

The amount of extract used will depend on the concentrations of bacterial material in the extract, but extracts based on a concentration of from about $1\times10^9$ to about $1\times10^{10}$ cells can be employed in a concentration of from about 0.001 to about 50% by weight, preferably about 0.001 to about 30% by weight, more preferably from about 1 to about 20% by weight, of the total composition. *Lactobacillus* strains of any species generally recognized as safe can be used as the basis for the extract. Particularly preferred are extracts derived from *L. plantarum*.

The defensin-inducing extracts may be useful in the reduction or prevention of growth of microbial populations on the skin. Compositions containing effective amounts (as described above) of *Lactobacillus* extracts are applied to the skin for this purpose on an as-needed basis, for example, to an open cut or wound, that may have been in contact with dirt or undesirable microbes, or on a chronic basis, applied to clean skin to maintain a healthy level of skin flora on a daily basis.

The extracts may also be useful as a preservative in cosmetic or pharmaceutical products. In particular, *Lactobacillus plantarum* extracts and fractions thereof exhibit a broad spectrum of activity against both gram positive and gram negative bacteria in vitro.

The extracts of the invention are also useful in the treatment of acne. Topical compositions containing *Lactobacillus plantarum* extract are shown to reduce the incidence of both inflamed and non-inflamed acne lesions when applied regularly over a period of six weeks. (see Example 5).

The extracts of the invention also are useful in the reduction skin sensitivity, as shown by reduction of lactic acid stinging (Example 6), when used regularly (twice daily) over a 2 month period.

The invention is further illustrated by the following non-limiting examples:

EXAMPLE 1

Procedure for the Fermentation of *Lactobacillus plantarum*

The *L. plantarum* organism is maintained at a final pH of 6.3.±.0.2 on Non-Animal MRS Agar with the following composition:

| Peptone | 10 gram/liter |
|---|---|
| Yeast Extract | 20 |
| Glucose | 20 |
| Tween 80 | 1.08 |
| Dipotassium Phosphate | 2 |
| Sodium Acetate | 5 |
| Ammonium Citrate | 2 |
| Magnesium Sulfate | 0.2 |
| Manganese Sulfate | 0.05 |

To make working MRS agar media, 55.3 g of powder is suspended in one liter of purified water and mixed thoroughly. The mixed heated with frequent agitation and boiled for one minute to completely dissolve the powder. The media is then sterilized by autoclaving at 121° C. for 15 minutes.

Characteristics of *Lactobacillus plantarum*

The *L. plantarum*, harvested is in the form of straight rods with rounded ends, generally 0.9-1.2 microns wide and 3-8 microns long. The organism occurs singly in pairs or short chains. The biochemical characteristics of *L. plantarum* are illustrated in Table 1.

TABLE 1

| Characteristics of *Lactobacillus plantarum*, | |
|---|---|
| Mortality | − |
| Gram's Stain | + |
| Casein digested | +* |
| Indole Production | − |
| H$_2$S | .+−. |
| Catalase | − |
| Cytochrome | − |

TABLE 1-continued

| Characteristics of *Lactobacillus plantarum*, | |
|---|---|
| Benzidine reaction | − |
| Pigment | off white |
| Growth on solid media | + |
| Anaerobic Growth | + |
| Temp. Optimum | 30-40.degree. C. |
| pH optimum | 5.5 |

*Expected % positive strains showing a positive reaction after 48 hours at 37° C.

Fermentation

Having been harvested, the *L. plantarum* is grown anaerobically by fermentation. The *L. plantarum* organism is transferred with a sterile loop from a MRS slant and inoculated into a flask containing two liters of Non-Animal MRS broth media. The broth is incubated overnight at 37 degree C., with stirring to achieve good growth. The medium becomes turbid. The culture is then transferred to a solid medium and Gram stained to confirm the purity of the culture.

A 15 liter New Brunswick fermentor is filled with 10 liters of medium having the following recipe:

| Vegetable peptone | 20 gram/liter |
|---|---|
| Yeast Extract | 5 |
| Glucose | 20 |
| Tween 80 | 1.08 |
| Dipotassium Phosphate | 2 |
| Sodium Acetate | 5 |
| Ammonium Citrate | 2 |
| Magnesium Sulfate | 0.2 |
| Manganese Sulfate | 0.05 |

The fermentor and medium are sterilized for 15 minutes at 15 lbs. pressure at 121° C. The fermentor medium is added to de-ionized water and put in the fermentor, diluted to a volume of 10 liters, and sterilized at 17 psi at a 120° C. for 20 minutes. Ultra Pure Compressed Nitrogen is sparged into the fermentor to maintain a dissolved oxygen of 0 mm Hg at a flow rate of 1.5 L/min. After cooling to room temperature, the inoculum from the 2 liter flask is added aseptically to the 10 liters of medium in the fermentor. The fermentor temperature is brought to 30-32 degrees. C. with agitation at 150 rpm. The initial pH of the media is 6.0-6.2. The culture is incubated at 16-20 hours at 30-32° C. with a final pH of the mixture is 4.0-4.2 and a population density of $10^6$-$10^7$ cells per milliliter.

The fermentation solution is than passed through a Coil Heat Exchanger with heating and cooling sections. The broth is lysed by raising the temperature to 105-110° C. and than immediately cooled to 7-10° C. At this point all intact cells have been lysed. The ferment is than passed through a 0.22 micron Cross Flow Filtration Unit at a flow rate of 0.4 liters per minute and transferred to an auxiliary storage kettle at which time 0.5% Phenoxeyethanol is added as a preservative. The product is then stored in a sterile poly-lined container.

EXAMPLE 2

Introduction: *Lactobacillus plantarum* was grown under anaerobic conditions using the New Brunswick fermenter (10 liter volume) as described above, and designated MIC 1844. MIC 1844 was fermented for 24 hrs at 30° C. The bacteria were fractionated with the heat exchange (1 passage) as already described, and processed through the cross-flow filter, 0.22μ. The unprocessed ferment, heat exchange (no processing), filtrate and retentate were assayed on NHEKs for hBD-2 induction. The non-filterable cell debris recovered from the heat exchange and processed through the cross-flow was designated the retentate. The retentate was concentrated 7-fold by the filtration process. The final concentration of the unprocessed ferment was between 2.5 and $5.0 \times 10^{10}$ cells/ml. The filtered material recovered from the heat exchange and cross-flow filtration (metabolized media and soluble cell components) was designated the filtrate. The filtrate had the same concentration as the unprocessed heat exchange or the unprocessed ferment. All the fractions were boiled 20 minute prior to incubating with NHEKs. These precautions were warranted because viable bacteria proliferate extensively during the treatment of NHEKs, leading to contamination of the mammalian culture and a null result.

The concentration of the bacteria in the 1844 ferment was expected to be similar to the 1839 ferment, grown on a beef-based MRS broth, and stored for a period of three months at 4° C. Counts could not be determined before treating the NHEKs with the bacterial extracts. Therefore, the bacterial cell concentration was assumed to be similar.

Lipoteichoic acid (water-soluble) and peptidoglycans (water-insoluble) are the major cell wall components from gram-positive bacteria for inducing hDB-2 by NHEKs via the toll-like receptor. LPS or endotoxin is the major component of the outer membrane from gram-negative bacteria for inducing hBD-2. *Lactobacillus* lipoteichoic acids are probably present in the filtrate and contribute to the induction of hBD-2 mRNA in NHEKs. Likewise, *Lactobacillus* peptidoglycans are may be present in the retentate and may contribute to the induction of hBD-2 mRNA in NHEKs. This might explain why activity was found in both of these fractions.

Methods: NHEKs were grown in the presence of Cascade EPI Life. Cells were treated at 80-90% confluence. NHEKs were treated for 48 hrs and the RNA was harvested. *Lactobacilli* were grown in the presence of a bean extract provided by Solabia. This media was prepared from scratch. The *Lactobacillus* MRS broth from DIFCO contains peptone, beef extract, yeast extract, dextrose, sodium acetate and a selection of salts. In this recipe, the beef extract (10 g/liter) was replaced with the bean extract (10 g/liter) from Solabia. The unprocessed ferment, heat-exchange fraction, filtrate fraction and the retentate fraction from the 1844 experiment were compared with the 1839 fractions. The 1839 fractions were derived from *Lactobacilli* grown in MRS broth (beef extract) and heat-exchanged. The 4 fractions were kept at 4° C. for 3 months. *Lactobacilli* were grown in a 10L New Brunswick fermentor for 24 hrs at 30° C. The recovery from the 1844 ferment was $2.5-5 \times 10^{10}$ cells/ml. The 1839 ferment had approximately from $9 \times 10^{10} - 2.8 \times 10^{11}$ cells/ml. This translates into a 44-72% decrease in cell number when using the bean extract.

The 1844 unprocessed ferment was added to NHEKs seeded on 100 mm plates at 4 doses: $10^8$, $10^9$, $5 \times 10^9$ or $10^{10}$ bacteria. The heat-exchanged 1844 *Lactobacillus* extracts were added to NHEKs at 3 doses: $10^9$, $5 \times 10^9$ or $10^{10}$ bacteria. The 1844 filtrate was added at 4 doses: $10^9$, $5 \times 10^9$, $10^{10}$ or $5 \times 10^{10}$ bacteria. The 1844 retentate was added to NHEKs on 100 mm plates at 4 doses: $10^9$, $5 \times 10^9$, $10^{10}$ or $5 \times 10^{10}$ bacteria. Bacterial components smaller than 0.22µ were recovered in the filtrate after cross-flow filtration. Cellular debris larger than 0.22µ was recovered as the retentate after cross-flow filtration (four dose). Some of the bacterial fractions were acidic (pH between 3 and 4), causing the keratinocyte media to become yellow upon addition. The pH was immediately neutralized with up to 200 µl of 800 mM Hepes. Hepes was added to all the cultures. The 1839 bacterial extracts, which were stored at 4° C. for 3 months was included for comparison. The treatments were initiated before the bacterial counts were available and both ferments were assumed to reach the same bacterial concentration. Therefore, the same treatment volumes were included for the 1844 as used for 1839 (unprocessed ferment: 1, 10, 50 and 100µl; heat-exchange: 10, 50 and 100 µl; filtrate: 3.6, 18, 36 and 180 µl; retentate: 10, 50, 100 and 500 µl). All the bacterial extracts were boiled for 20 minutes.

Figure 1:
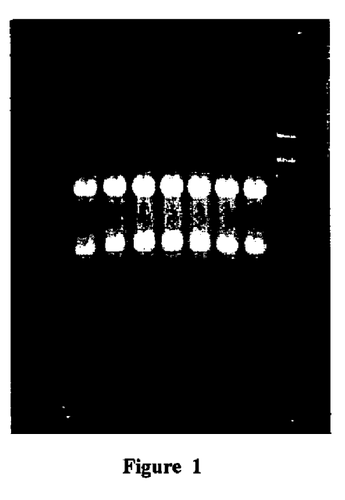
Figure 2:
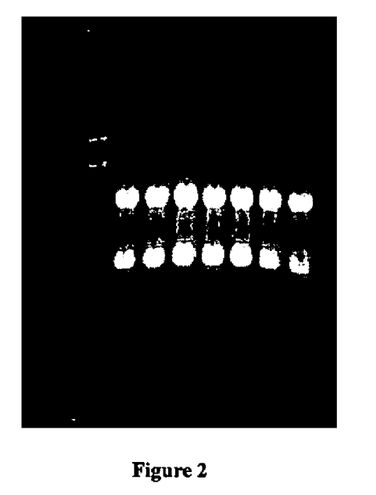

Total RNA was recovered with TRIzol reagent (Invitrogen). The concentration of the mRNA was determined with the RiboGreen kit (Molecular Probes) as well as by gel electrophoresis of selected samples. Several RiboGreen assays were run in order to evaluate each sample in duplicate or triplicate. The results were averaged (see Table 2). The amount of RNA degradation was evaluated on 2 gels (FIGS. 1 and 2). RNA was reverse transcribed into cDNA using the RETROscript kit from Ambion. The internal standard was 18S Ribosomal RNA. cDNA was amplified using the Light Cycler in conjunction with the FastStart DNA Master SYBR Green 1 kit from Roche. Primers specific for 18S ribosomal RNA and hBD-2 were previously described. For 18S ribosomal RNA, 100 ng of template were amplified for 40 cycles. For hBD-2, 300 ng of template were amplified for 40 cycles. The number of PCR products having different molecular weights generated by the PCR reaction was determined indirectly with a melting curve program from Roche. A single melting point peak was observed for each primer set.

Figure 3:
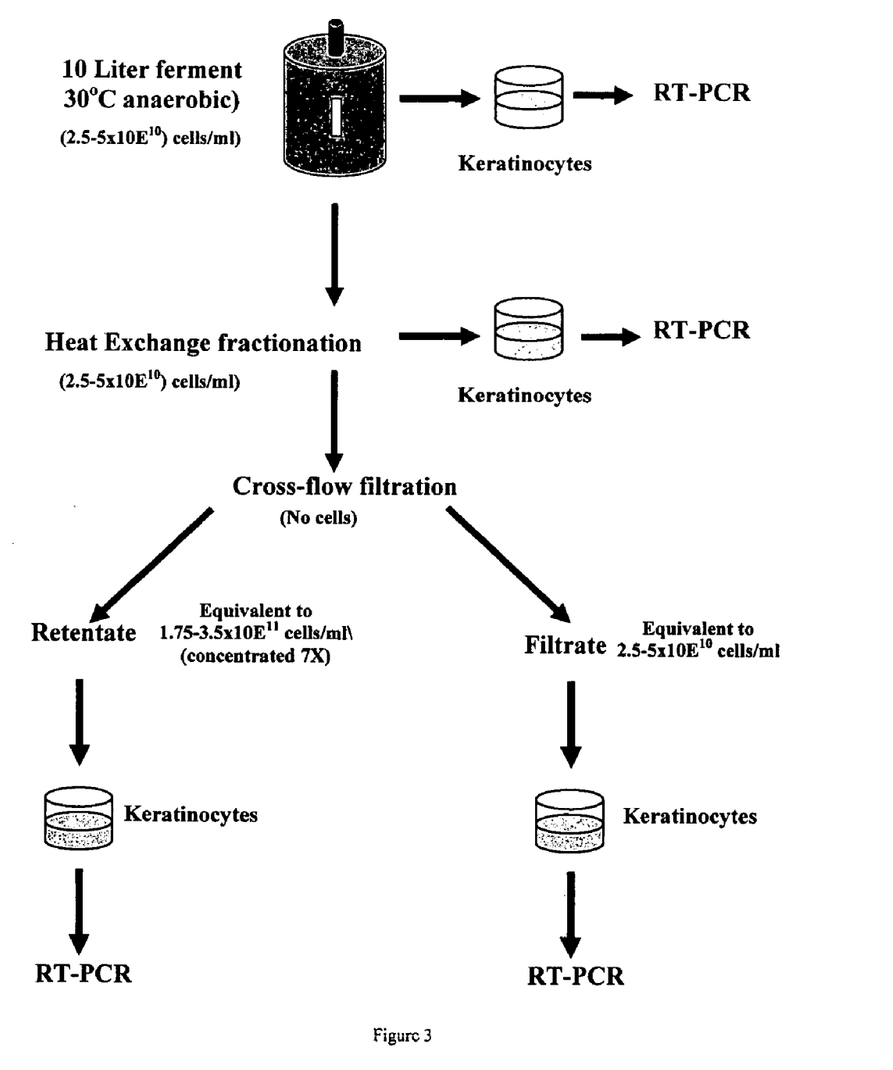
FIG. 3 is flow chart illustrating the preparation of various fractions of *Lactobacillus* extract.

Results and Conclusion: Total RNA levels were measured with a fluorescent probe specific for RNA (RiboGreen ELISA) (Table 1). Visual quantitation of the ribosomal 28S RNA band was determined for a select group of samples (FIGS. 1 and 2). No RNA degradation was observed. The intensity of the 28S Ribosomal RNA band (top band) varied slightly (783000±25000) (FIG. 1) and 882000±46000, (FIG. 2). The intensity of the bands for both gels was restricted to a pixel area of 8000.1 was successful at amplifying 18S ribosomal mRNA (lower band) as an internal control. No external control was included to measure the efficiency of reverse transcription. A flow chart representing the different fractions is present in FIG. 3.

Figure 4:
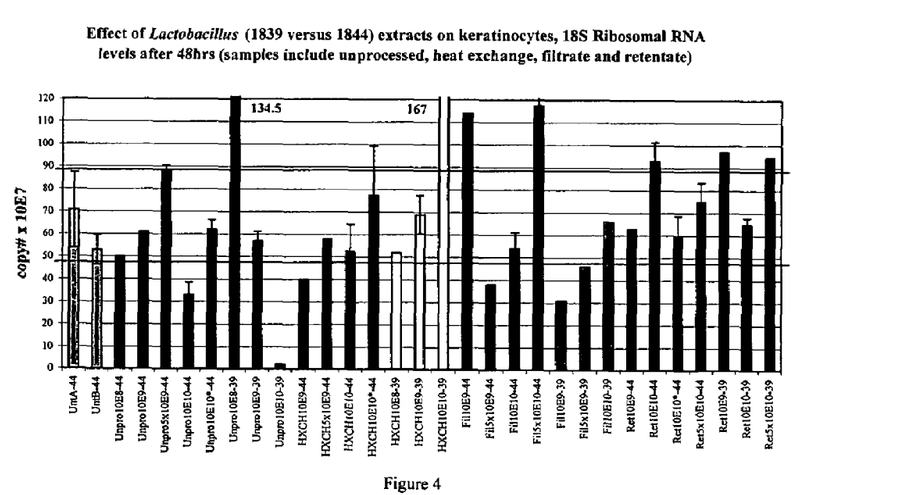

Most of the *Lactobacillus* extracts used to treat NHEKs generated 18S ribosomal mRNA levels within the range of the untreated samples (FIG. 4). In most cases, a dose-dependent increase in 18S ribosomal mRNA levels was observed, suggesting the extract induced proliferation. The strongest increase in 18S ribosomal mRNA was observed with the 1839 heat-exchange sample, 10E10 bacteria. An exception included the 1839 ferments, which showed a dose-dependent decline in 18S ribosomal mRNA levels. A decline in 18S levels is usually a sign of cellular stress of some nature and appears related to the extract since it was dose-dependent. The decline in 18S mRNA levels could be explained by a decline in NHEK proliferation or increased NHEK death. In general, the 18S ribosomal mRNA levels stayed within the standard deviation of the untreated control but appeared to increase slightly in a dose-dependent manner.

Figure 5:
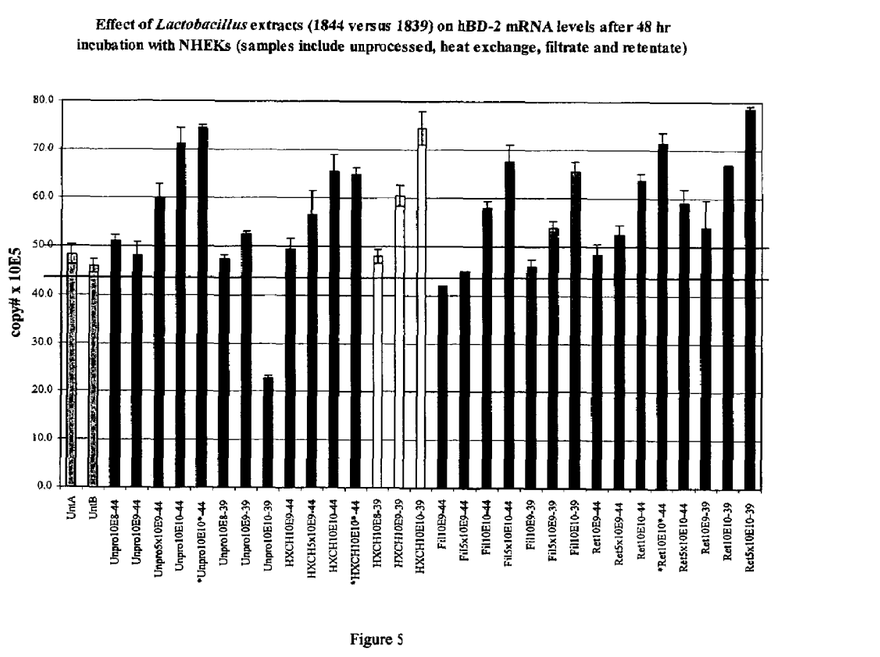

All the 1844 *Lactobacillus* extracts induced a dose-dependent increase in hBD-2 mRNA levels in NHEKs. The unprocessed ferment, heat-exchange, filtrate or retentate induced hBD-2 mRNA levels when a dose equivalent to $5 \times 10^9$ to $10^{10}$ bacteria was used. The 1844 retentate and 1844 filtrate required a slightly higher dose of bacteria as compared to the heat-exchange or the unprocessed ferment to induce hBD-2 mRNA (FIG. 5).

Figure 6:
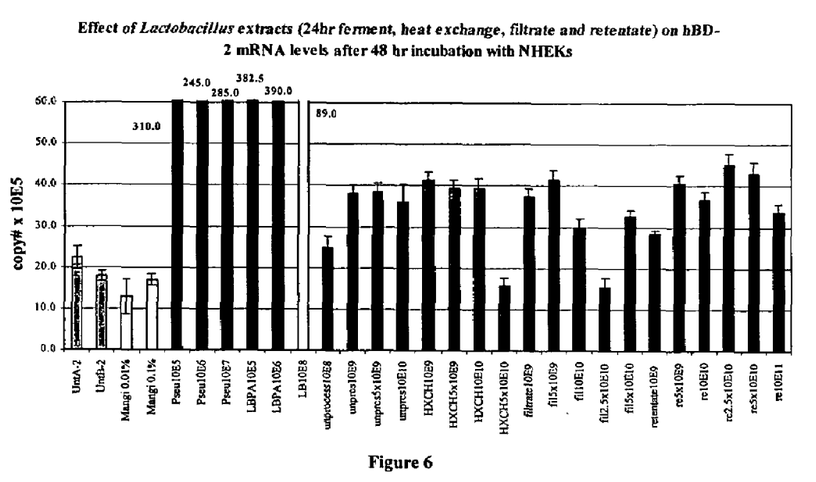

In conclusion, all the *Lactobacillus* extracts from the 1839 experiment or 1844 experiment had activity. Even the 1839 ferments, which had low 18S ribosomal mRNA levels, managed to produce hBD-2 mRNA levels, although the highest dose declined significantly. All the 1839 fractions retained activity despite being in storage for 3 months at 4° C. The hBD-2 mRNA levels for the 1839 fractions were comparable to earlier data on MIC1839 (average of $35\times10^5$ copies versus average of $55\times10^5$ copies). The difference can be accounted for by the increase in hBD-2 mRNA levels in the untreated sample ($20\times10^5$ versus $45\times10^5$ copies). Thus, they were fairly similar (see FIG. 6 for comparison). Fewer *Lactobacilli* were recovered from the 1844 ferment as compared to the 1839 ferment, approximately, a 44-72% decrease. The bean extract did not appear to significantly reduce the induction of hBD-2 mRNA despite this decrease in bacterial counts. The 1844 retentate was assumed to be concentrated in the same manner, as previously done for the 1839 ferment, therefore a 7-fold concentration factor was used. The assay appears to be reproducible since duplicate treatment samples processed in parallel gave values which were within the standard deviation for two treatment sets (1844 ferment and 1844 heat-change) and not for a third treatment set (1844 retentate). The overall increase in hBD-2 mRNA levels was small but significant. This data set demonstrates that cross-flow filtration does not increase the activity of the sample, since the filtrate and the retentate had similar levels of mRNA induction and slightly less than the ferment. Therefore, at least two different inducers of hBD-2 mRNA are present. The inducers are probably the lipoteichoic acids in the filtrate and the peptidoglycans in the retentate. All the 1844 extracts caused a dose-dependent increase in hBD-2 mRNA levels.

Subjects

A total of nine subjects, male and female the age of 25-55 participate in the study. All subjects are in normal health with no evidence of acute or chronic disease and/or dermatologic or ophthalmological problems. Subjects exhibiting current sunburn, rashes, scratches, burn marks etc., which might interfere with evaluation of test results are excluded from the study. Pregnant or lactating females are excluded. The test site is devoid of warts nevi, moles, sunburn, suntan, scars and active dermal lesions observed upon observation.

Procedure

Skin Microflora

The panelists report to the laboratory and wash their faces with a mild liquid soap. The right side of the face is treated with the vehicle and the left side with the formulation containing *lactobacillus* extract. The materials are applied and blended in by the investigator, using sterile gloves. The normal microflora is allowed to appear on the skin in the next three hours. During this period the panelists are advised to keep their hair away from the face and refrain from touching the face or wash it or apply anything on it. At the end of this three hour time point, saline washings are obtained from the cheek area of the face for microbiological analysis.

TABLE 2

Quantitation of total RNA derived from NHEKs treated for 48 hrs with *Lactobacillus* ferment containing beef (1839) and bean (1844)

| Samples (MIC 1844) | Ribo-Green μg/μl | Avg. | # of μls equivalent to 4 μgs of RNA |
|---|---|---|---|
| #1 NHEK untreated A 48 hrs | 2.96/3.03 | 3.00 | 1.33 |
| #2 NHEK untreated B 48 hrs | 2.62/2.65 | 2.64 | 1.52 |
| #3 NHEK 1844 ferment 10E8 48 hrs | 2.62/2.72/2.65 | 2.66 | 1.50 |
| #4 NHEK 1844 ferment 10E9 48 hrs | 2.71/2.75/2.76 | 2.74 | 1.46 |
| #5 NHEK 1844 ferment 5 × 10E9 50 μl 48 hrs | 2.73/2.63/2.59 | 2.65 | 1.51 |
| #6 NHEK 1844 ferment 100 μl 10E10 48 hrs | 2.34/2.72 | 2.53 | 1.58 |
| #7 NHEK 1844 retentate 10E9 10 μl 48 hrs | 2.86/2.80/2.92 | 2.86 | 1.40 |
| #8 NHEK 1844 retentate 5 × 10E9 48 hrs | 2.62 | 2.62 | 1.53 |
| #9 NHEK 1844 retentate 10E10 48 hrs | 2.82/3.05/3.01 | 2.96 | 1.35 |
| #10 NHEK 1844 retentate 5 × 10E10 48 hrs | 2.52 | 2.52 | 1.59 |
| #11 NHEK 1844 filtrate 10E10 48 hrs | 2.31/2.30 | 2.31 | 1.73 |
| #12 NHEK 1844 filtrate 5 × 10E10 180 μl 48 hrs | 2.26/2.10 | 2.18 | 1.83 |
| #13 NHEK 1844 HXCH 10E10 100 μl 48 hrs | 2.59/2.60 | 2.60 | 1.54 |
| #14 NHEK 1844 HXCH 5 × 10E9 50 μl 48 hrs | 2.69/2.55 | 2.62 | 1.53 |
| #15 NHEK 1844 HXCH 10E9 10 μl 48 hrs | 2.61/2.71 | 2.66 | 1.50 |
| #16 NHEK 1839 ferment 10E8 48 hrs | 2.83/3.26 | 3.05 | 1.31 |
| #17 NHEK 1839 ferment 10E9 48 hrs | 2.88/3.01 | 2.95 | 1.36 |
| #18 NHEK 1839 ferment 10E10 48 hrs | 2.88/2.88 | 2.88 | 1.39 |
| #19 NHEK 1839 retentate 10E9 48 hrs | 2.96/2.96 | 2.96 | 1.35 |
| #20 NHEK 1839 retentate 10E10 48 hrs | 3.26/3.26 | 3.26 | 1.23 |
| #21 NHEK 1839 retentate 5 × 10E10 48 hrs | 2.32 | 2.32 | 1.72 |
| #22 NHEK 1839 filtrate 10E9 48 hrs | 2.61/2.76 | 2.69 | 1.49 |
| #23 NHEK 1839 filtrate 5 × 10E9 48 hrs | 2.27/2.59 | 2.43 | 1.65 |
| #24 NHEK 1839 filtrate 10E10 48 hrs | 2.46/2.65 | 2.56 | 1.56 |
| #25 NHEK 1839 filtrate 5 × 10E10 48 hrs | 2.12/2.10 | 2.11 | 1.90 |
| #26 NHEK 1839 HXCH 10E8 48 hrs | 2.76/3.05 | 2.91 | 1.37 |
| #27 NHEK 1839 HXCH 10E9 48 hrs | 3.06/3.06 | 3.06 | 1.31 |
| #28 NHEK 1839 HXCH 10E10 48 hrs | 2.76/2.82 | 2.79 | 1.43 |

EXAMPLE 3

A clinical study is designed to study skin microflora after one treatment with *Lactobacillus* extract which is claimed to stimulate the release of defensins. The materials tested are a Carbopol gel vehicle without *Lactobacillus*, and a Carbopol gel vehicle containing 20% *Lactobacillus* extract (each pH 3.90).

Saline (Dulbeccos Phosphate Buffered Saline) washings of the forehead area are obtained using a sterile glass cylinder and a sterile rubber policeman. One ml of the saline wis poured in the cup and then skin is scrubbed with rubber policeman (10 strokes) and washed and then the saline is aspirated and collected in 9 mls of PBS. The samples are analyzed for aerobic and anaerobic bacterial count.

Results

Figure 7:
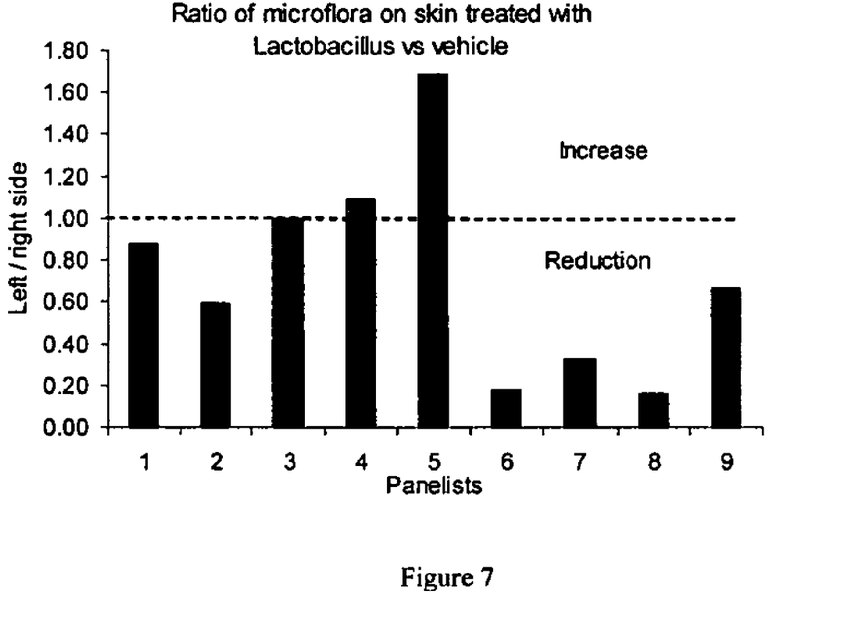
FIG. 7 illustrates the effect of *Lactobacillus* extracts on the amount of microflora on the skin.
Figure 8A:
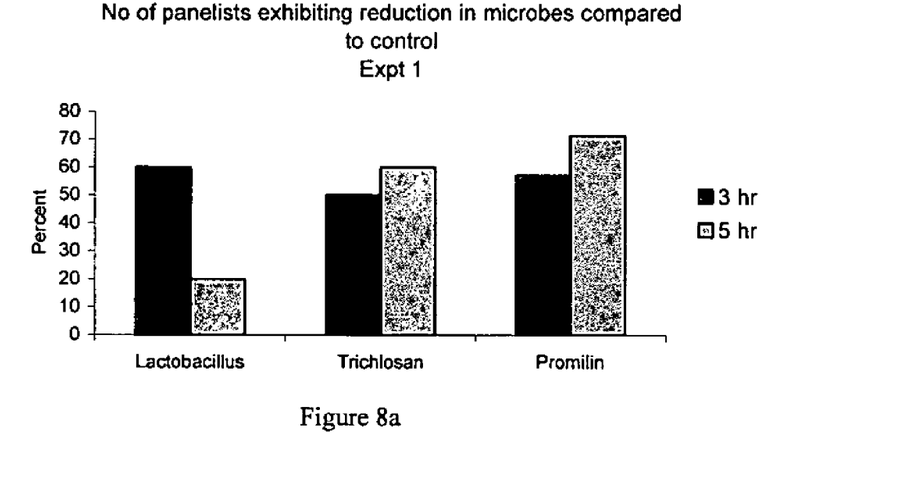
FIG. 8 illustrates the effect of *Lactobacillus* extracts on skin microflora compared with antimicrobial/defensin stimulators Triclosan and promillin.
Figure 8B:
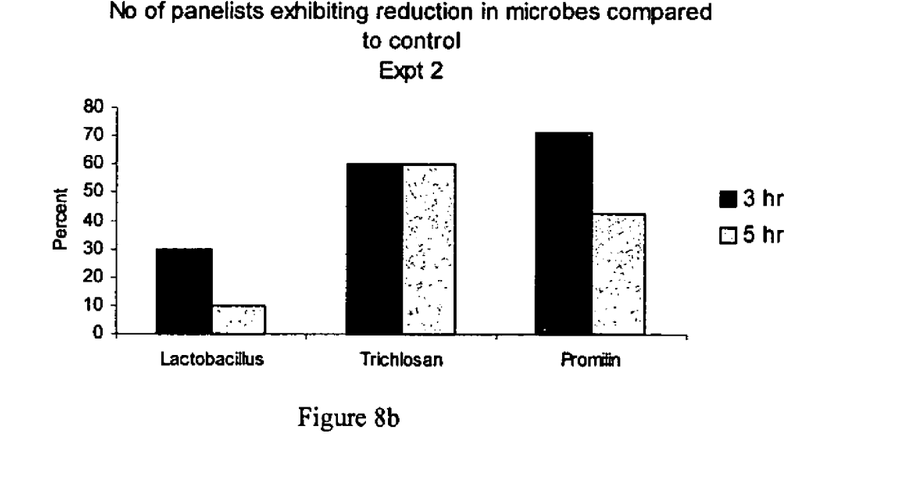

The graph in FIG. 7 exhibits the ratio between the *Lactobacillus* vs vehicle treated sites for each panelist. A value of 1 indicates no difference, while values below 1 indicate a reduction in bacterial growth on the *lactobacillus* treated site. As observed in the graph, 20% *lactobacillus* extract was effective in reducing bacterial growth on skin. Six panelists out of nine exhibited a reduction in microbial growth, 3 hours after treatment. One panelist exhibited no change and two exhibited higher growth with the 20% *lactobacillus* extract.

EXAMPLE 4

Several different fractions of *Lactobacillus plantarum* extract are tested for their ability to inhibit bacterial and fungal growth. The fractions are 1-supernatant fraction; 2-concentrated cellular fraction; 3-concentrate whole broth; 4-unconcentrated; 5-unconcentrated on vegetable broth media; and 6-distilled water control.

Method:

The several organisms chosen for this experiment are picked for their diversity and relevance in cosmetic preservative testing. The organisms include *Escherichia coli* (EC), *Klebsiella pneumonie* (KP), *Pseudomonas aeruginsa* (PA), *Pseudomonas cepacia* (PC), *Staphylococcus aureus*(SA), *Staphylococcus epidermidis* (SE), *Candida albicans* (CA), *Candida parapsilosis* (CP) and *Aspergillus niger* (AN).

The individual bacterial cultures (EC, KP, PA, PC, SA and SE) are streaked onto Trypticase Soy Agar (TSA) plates and the fungal cultures (CA, CP and AN) were streaked onto Potato Dextrose Agar (PDA). A cork borer (#5) is used to make a well in the middle of each plate, and 200μl aliquot of each sample was added to the individual wells for each individual organism. The plates are then incubated at 37° C. for 48 hours. After this time, the plates are examined and zones of inhibition (if any) were observed. The zones are measured in millimeters from the edge of each well.

Results:

MIC Zones of *Lactobacillus* ferment: (See Above for Organism and Sample description). A zone of inhibition>2 mm is considered significant activity

|  | EC | KP | PA | PC | SA | SE | CA | CP | AN |
|---|---|---|---|---|---|---|---|---|---|
| No. 1 | 3 | 3 | 3 | 3 | 5 | 3 | 0 | 0 | 0 |
| No. 2 | 2 | 2 | 4 | 4 | 4 | 7 | 1 | 0 | 1 |
| No. 3 | 5 | 5 | 6 | 5 | 7 | 7 | 3 | 3 | 0 |
| No. 4 | 2 | 2 | 1 | 3 | 2 | 3 | 0 | 0 | 0 |
| No. 5 | 3 | 3 | 2 | 4 | 6 | 3 | 1 | 1 | 0 |
| No. 6 | 0 | 0 | 0 | 0 | 0 | 0 | 0 | 0 | 0 |

Conclusion:

Five fractions of *Lactobacillus* are evaluated for their antimicrobial activity against several microorganisms commonly used for the Preservative Efficacy Testing of cosmetic products. All displayed a significant level of activity against both gram negative and gram positive bacteria. Little or no activity was observed against yeast and mold.

EXAMPLE 5

An anti-acne lotion having the following formula is tested to determine its ability to reduce inflamed and non-inflamed acne lesions.

| Material | Weight % |
|---|---|
| Distilled water | QS |
| Sodium EDTA | 0.100 |
| Quaternium 22 | 0.100 |
| Sclerotium gum | 0.500 |
| Ceteareth 20 | 2.500 |
| Butylene glycol | 5.000 |
| Polymethyl methacrylate | 1.000 |
| Zeolite | 0.500 |
| Cyclopentasiloxane | 10.500 |
| Dimethicone(100 cts) | 2.000 |
| Myristyl alcohol | 0.750 |
| Sodium hyaluronate | 2.000 |
| Algae extract(Alguard) | 0.900 |
| Bisabolol | 0.050 |
| Tocopheryl acetate | 0.100 |
| Preservative | 1.000 |
| Colorant | 0.0042 |
| Acrylamide/sodium acryloyldimethyl taurate copolymer/isohexadecane/polysorbate 80 | 2.000 |
| colorant | 0.0080 |
| *Lactobacillus* solution | 10.000 |

Figure 9A:
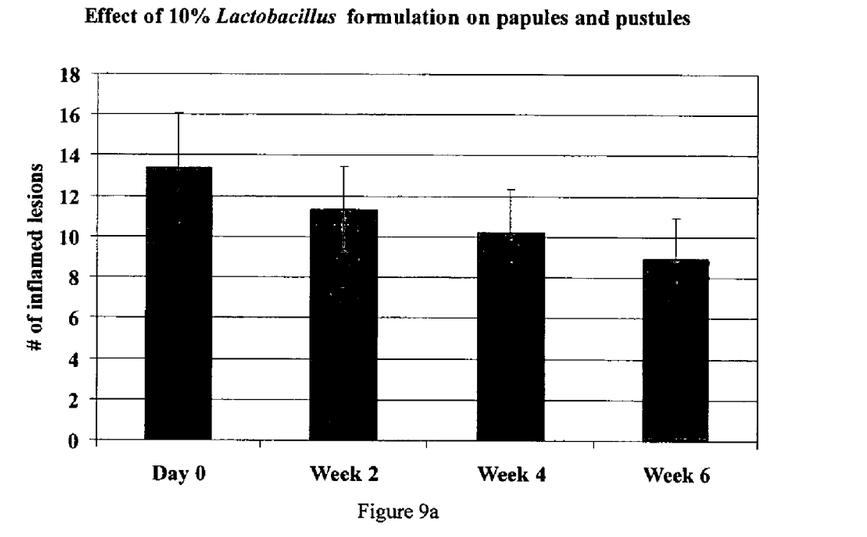
FIG. 9 illustrates the effect of a composition containing 10% *Lactobacillus* solution on (a) acne papules and pustules and (b) acne open and closed comedones, over a six-week period.
Figure 9B:
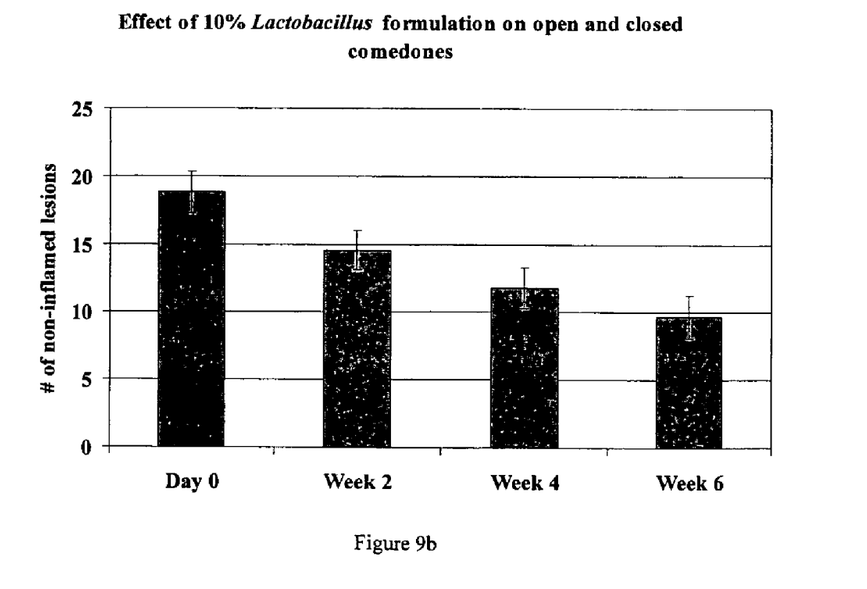

After a six-week trial, the composition is shown to significantly (p<0.0001) reduce both inflamed lesions and non-inflamed lesions. The results are shown graphically in FIG. 9.

EXAMPLE 6

A clinical study is conducted to study skin sensitivity after 2 month treatment with materials that stimulate the release of defensins, namely *Lactobacillus* extract and Alguard. The study is conducted with three test products, each in an identical base; the tested materials are a (1) *Lactobacillus* Ferment (*Lactobacillus plantarum*) at 1% (derived from fragmented *lactobacillus* at less than 0.22 u in size); (2) Trichlosan (an antibacterial) at 0.1% (control); and (3) Alguard (Poly sea) which is a bioexudate of red algae (*porphyridium* sp; Rhodophyta) at 1%. It contains 1% polysaccharide and is claimed to exhibit anti-irritant properties.

Subjects

A total of twenty nine females between the age of 25-55 participate in the study. The panel is divided in three groups of 9-10 each. All subjects were in normal health with no evidence of acute or Chronic disease and/or dermatologic or ophthalmological problems.

Subjects exhibiting current sunburn, rashes, scratches, burn marks etc., which might interfere with evaluation of test results were excluded from the study. Pregnant or lactating females were excluded. The test site was devoid of warts nevi, moles, sunburn, suntan, scars and active dermal lesions observed upon observation.

Procedure

Treatments

The panel is divided in three groups of 9-10 each corresponding to the test materials. The panelists are provided with a cream to use twice a day for two months on the full face and left forearm. The right arm is the untreated control. They are instructed not to use any other moisturizers or treatment products, however they could continue to use the cleansers and makeup that they normally use as long as they do not change products. On the day of the study the panelists are instructed to report to the lab with a clean face and forearms, with no creams, lotions, makeup etc. Measurements of lactic acid stinging on the panel are obtained at baseline, 1 month and 2 month. Ten percent lactic acid is applied on one side of the face and saline on the other side (Frosch and Kligman, *J Soc*

*Cosmet Chem,* 28:197-209, 1977). Sting intensity as reported by the panelists is documented after 2.5 minutes and 5 minutes. Cumulative sting intensity is the sum of the sting intensity on the lactic acid treated site subtracted by the sum of the sting intensity on the saline treated site. After 1 and 2 months treatment the panelists are tested with lactic acid again. On the day of the test the panelists do not apply the product. The difference between the sting intensity of baseline versus 4 week treatment was calculated.

Figure 10:
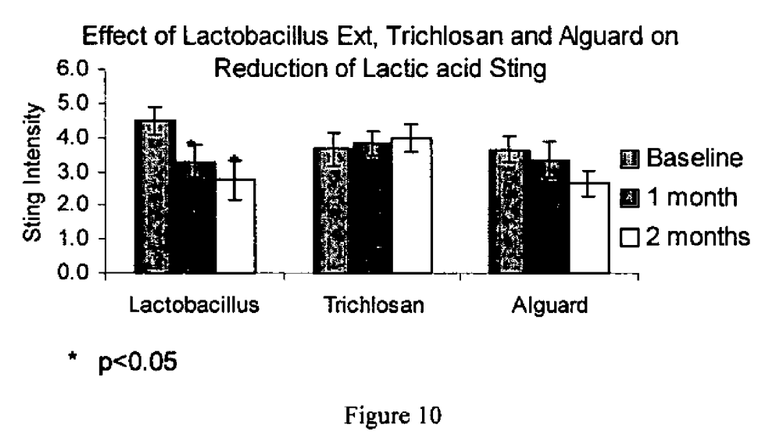
FIG. 10 illustrates the effect of *Lactobacillus* extract on lactic acid stinging, compared with Trichlosan and Alguard.

FIG. 10 exhibits the cumulative sting scores of the panel. It is clear from the graph that *Lactobacillus* extract is significantly effective in reducing lactic acid induced sting. After 1 month and two months of use there is 27% (p=0.035) and 39% (p=0.009) reduction in stinging, respectively. Alguard exhibits 8% (p=0.53) and 27% (0.058) reduction in stinging after one and two month use, respectively. Trichlosan appears to be irritating on skin, since sting response increased after using this material.

What we claim is:

1. A method of stimulating beta-defensins in skin cells which comprises applying to the skin cells an effective amount of a *Lactobacillus plantarum* extract or active fraction thereof selected from the group consisting of: (a) a heat exchange-treated *Lactobacillus plantarum* ferment comprising broken up cells of *Lactobacillus plantarum*; (b) a filtrate fraction of a heat exchange-treated *Lactobacillus plantarum* ferment, wherein said filtrate fraction comprises water soluble cellular debris of *Lactobacillus plantarum*; (c) a retentate fraction of a heat exchange-treated *Lactobacillus plantarum* ferment, wherein said retentate fraction comprises water-insoluble cellular debris of *Lactobacillus plantarum*; and (d) one or more combinations of said extracts or fractions.

2. The method of claim 1 in which the *Lactobacillus plantarum* extract is a heat exchange-treated *Lactobacillus plantarum* ferment comprising broken up cells of *Lactobacillus plantarum*.

3. The method of claim 1 in which the active fraction of the *Lactobacillus plantarum* extract is a filtrate fraction of a s-heat exchange-treated *Lactobacillus plantarum* ferment filtered on a 0.22 filter.

4. The method of claim 1 in which the active fraction of the *Lactobacillus plantarum* extract is a retentate fraction of a s-heat exchange-treated *Lactobacillus plantarum* ferment filtered on a 0.22 filter.

* * * * *